US00PP32068P2

(12) United States Plant Patent
Hansen

(10) Patent No.: US PP32,068 P2
(45) Date of Patent: Aug. 11, 2020

(54) ***HOSTA* PLANT NAMED 'MISS AMERICA'**

(50) Latin Name: ***Hosta* hybrid (Tratt.)**
Varietal Denomination: Miss America

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,620

(22) Filed: Nov. 8, 2019

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 6/12; A01H 6/56
See application file for complete search history.

*Primary Examiner* — June Hwu

(57) ABSTRACT

A new and distinct *Hosta* plant named 'Miss America' with large, rounded-mound habit of heavy-substance, stiff, variegated foliage. Leaves are shiny, flat, cordate with creamy-white centers and broad, deep green margins and intermediate colors between. Flowers have white margins with pale lavender center stripes on tepal insides and are held on stiff, upright cream-colored stems with about 90 flowers per scape.

2 Drawing Sheets

Latin name and variety denomination of the plant:
Botanical classification: *Hosta* hybrid (Tratt.).
Variety denomination: 'Miss America'.

STATEMENT REGARDING PRIOR DISCLOSURES UNDER 37 CFR 1.77(B)(6)

*Hosta* 'Miss America' was first introduced by the inventor as a non-enabling description through the International Cultivar Registration Authority registration in early 2019. No plants of *Hosta* 'Miss America' have been sold, in this country or anywhere in the world, nor has any disclosure of the new plant been made, more than one year prior the filing date of this application.

BACKGROUND AND ORIGIN OF THE PLANT

The present invention relates to a new and distinct *hosta* plant, *Hosta* 'Miss America' hereinafter also referred to as the new plant or just the cultivar name, 'Miss America'. *Hosta* 'Miss America' was a cross on Jul. 29, 2013 by the inventor at a wholesale perennial nursery in Zeeland, Mich., USA between the non-patented, unreleased, proprietary sport known only as 'American Sweetheart Streaked' as the female parent and 'Elatior' (not patented) as the male parent. The new plant was assigned the breeder code 13-151-1 and passed the initial evaluation in the summer of 2015. The new plant has been asexually propagated by division at the same nursery in Zeeland, Mich., USA since 2017 and also by careful plant shoot-tip tissue culture with the resultant asexually propagated plants having retained all the same traits as the original plant.

BRIEF SUMMARY OF THE PLANT

There are nearly 6,000 registered *hosta* cultivars with The American *Hosta* Society, which is the International Cultivar Registration Authority for the genus *Hosta* along with a similar number of unregistered cultivars. The nearest known comparison cultivars are *Hosta* 'American Sweetheart' (not patented), 'Ann Kulpa' (not patented), (U.S. Plant patent application Ser. No. 13/998,975, now abandoned), 'Night before Christmas' (not patented), 'Sea Thunder' (not patented) and 'Vulcan' (not patented).

All of the above plants have a green margin and a lighter variegated center. 'American Sweetheart' has a smaller habit with smaller leaves and the flowers are deeper lavender compared with the new plant has whiter margins on the flower tepals and a pale lavender longitudinal stripe. 'Ann Kulpa' has smaller more compact habit with smaller leaves and the smaller flowers are pure white with wider, more overlapping tepals. 'Cool as a Cucumber' has smaller habit with narrower, more lanceolate, arching foliage with more color distinctions between the margin and center and the flowers are a paler lavender to near white. 'Night before Christmas' has a smaller habit with more arching ovate-shaped leaves with more acute apices, wider centers and narrower margins and the flowers are more drooping and narrower at the apex with deeper lavender tepals. 'Sea Thunder' a smaller more arching habit, the foliage is smaller, more drooping and flexible, with narrower green margins and broader centers and the flowers are smaller, narrower and deeper lavender. 'Vulcan' has a smaller habit, smaller foliage with narrower margins and broader centers and the flowers are deeper lavender. The female parent has leaves that are irregularly streaked creamy white and deep green in a mericlinal chimera pattern and has a smaller habit with smaller leaves and the flowers are deeper lavender compared. The male parent has a larger habit with larger, light green leaves and with scapes that are more arching. The new plant has taller, more stiffly upright scapes than all of the above.

Other *Hosta* cultivars have variegated foliage, but 'Miss America' is distinct from the above listed *hostas* and all other cultivars known to the discoverer by the following combined traits:

1. Large-sized, round-mounded plant habit with heavy-substance, stiff, variegated foliage;
2. Heavy-substance, stiff leaves of cordate shape and acute apex and cordate base;
3. Very-broad deep-green margins with creamy white centers and intermediate colors between;
4. Leaves are flat, slightly shiny surface above and below;
5. Large flowers are both long and broad on strongly upwardly projecting scapes well above foliage;
6. Tepals have narrowly acute apices with near white margins, single longitudinal pale lavender stripe.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
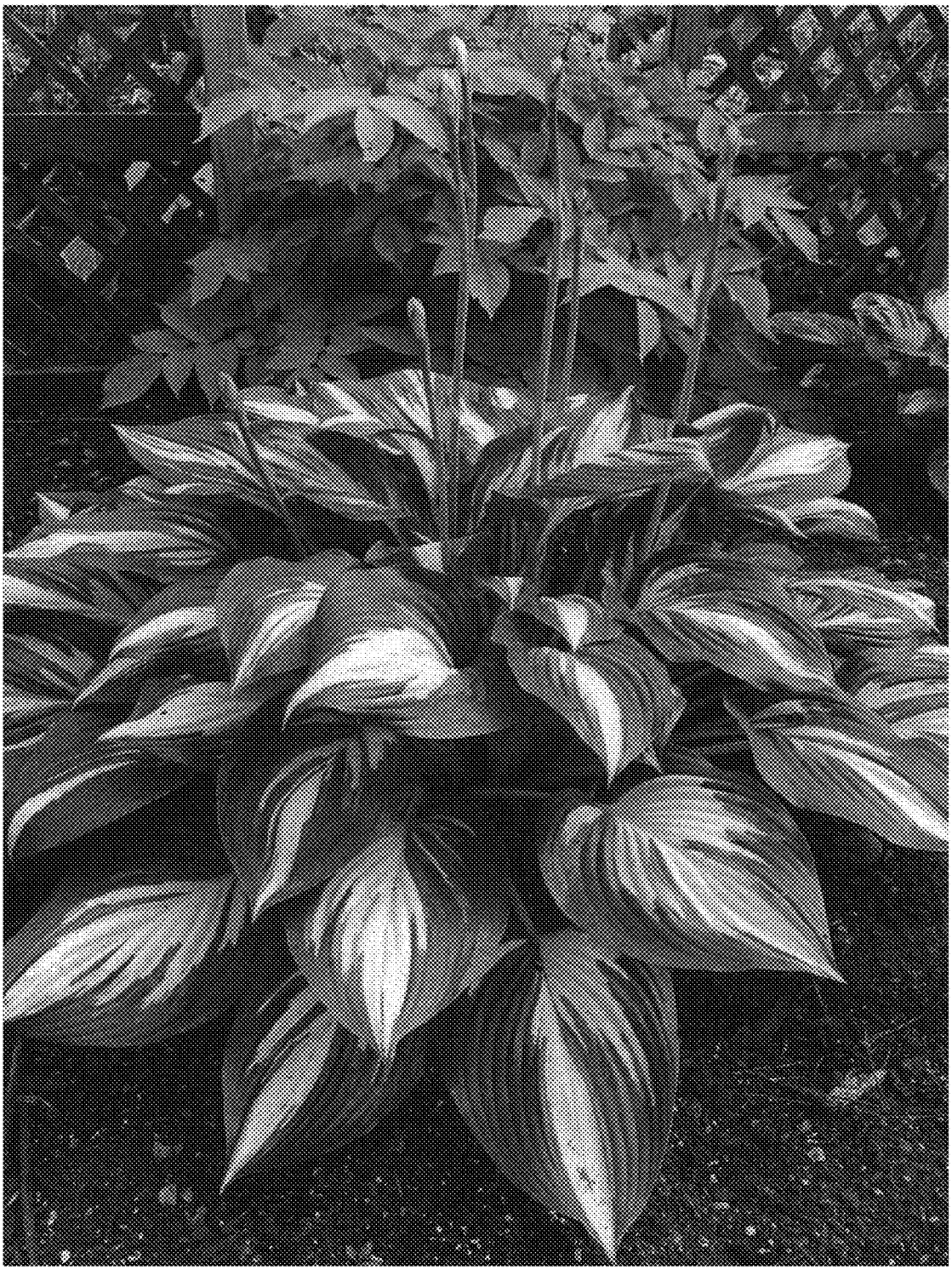
FIG. 1 shows a five-year-old plant with upright young scapes.
Figure 2:
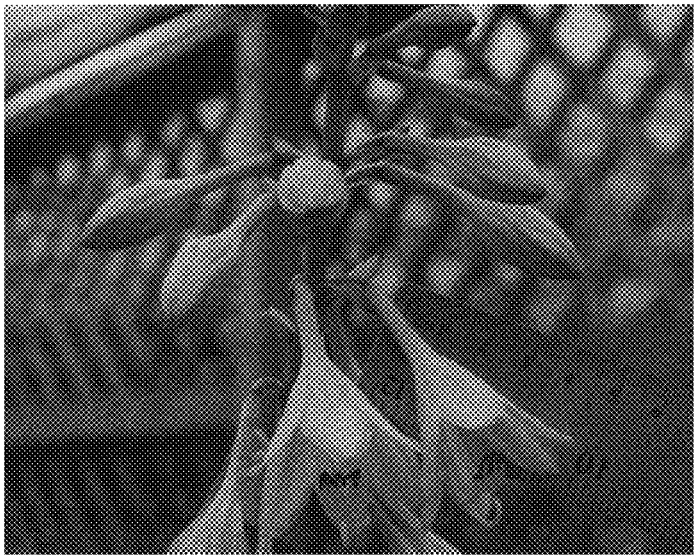
FIG. 2 shows a close-up of the flowers and buds.
Figure 3:
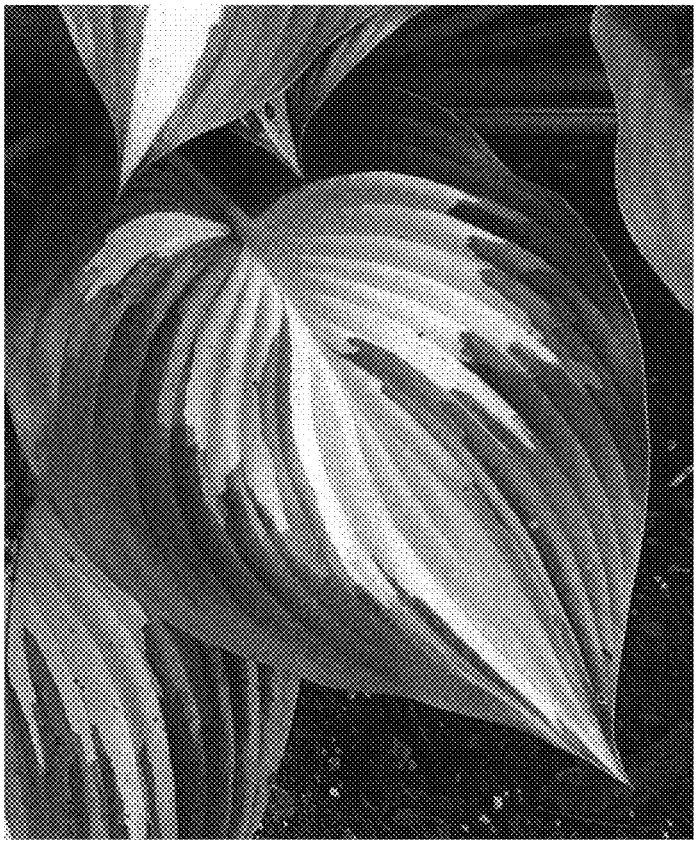
FIG. 3 shows a close-up of the foliage with variegation.

The following descriptions and color references are based on the 2015 edition of The Royal Horticultural Society Colour Chart except where common dictionary terms are used. The new plant, *Hosta* 'Miss America', has not been observed under all possible environments. The phenotype may vary slightly with different environmental conditions, such as temperature, light, fertility, moisture and maturity levels, but without any change in the genotype. The following observations and size descriptions are of a five-year old plant in a partially shaded trial garden in Zeeland, Mich. with supplemental water and fertilizer.

Botanical classification: *Hosta* hybrid;

Parentage: 'American Sweetheart Streaked' as the female parent and 'Elatior' as the male parent;

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color between RHS NN155A and RHS NN155B;

Plant shape and habit: Hardy herbaceous perennial with basal rosettes of leaves emerging from rhizomes producing a large, symmetrical, rounded-mound of leaves; about 8 divisions per plant; divisions to about 3.5 cm diameter at soil level;

Plant size: Foliage height about 77.0 cm above soil line to the top of the leaves and about 124.0 cm wide at the widest point about 35 cm above the soil line;

Foliage description: Ovate; acute apex; cordate base; entire margin; glabrous; moderately lustrous adaxial, abaxial beginning season slightly glaucous becoming strongly lustrous mid-season; blades mostly flat without twisting or without sinuate margin; with a thick stiff feel;

Leaf blade size: To about 35.0 cm long, 24.0 cm wide at base; average about 33.0 cm long and 21.5 cm wide;

Leaf blade color: Early season and expanding margin adaxial nearest RHS 138B and abaxial margin between RHS 138B and RHS 138C, adaxial center nearest RHS 155A with intermediate colors comprising nearest RHS 145A, RHS 146D and RHS 194C, abaxial center nearest RHS 155A with intermediate colors comprising RHS 145B, RHS 146D and RHS 193C; mid-season and later summer adaxial margin nearest RHS 137A, center variable between a blend between RHS 150D and RHS 158D to RHS NN155A, intermediate region variable comprising RHS 146B, blends between RHS 144A and RHS 146D, between RHS 146D and RHS 145D and between RHS 147C and RHS 149D; mid-season and later abaxial margin nearest RHS 137B, center nearest RHS 158D and intermediate comprising a blend between RHS 146D and RHS 145A, and blends between RHS N138D and RHS 192A and between RHS 193B and RHS 158D;

Petiole: Entire, glabrous, concavo-convex; stiff; mostly straight from base of plant to leaf base with little bending or curving, strong and slightly flexible; concavo-convex, deeply channeled; to about 21.5 cm long and 25.8 cm wide at base;

Petiole color: Adaxial margin about 3.5 mm wide blend between RHS 145A and RHS 144A near base and distally nearest RHS 137B, center with thin stripes less than 1.0 mm across nearest RHS 4D starting at blade and starting about three-quarters of the way to base nearest RHS 143A; abaxial margin nearest RHS 143A, center nearest RHS NN155A with multiple stripes less than 1.0 mm across nearest RHS 145A, basal 4.0 cm maculate with tiny spots about 0.2 mm diameter nearest RHS 187D;

Veins: Parallel, lightly impressed adaxial, moderately bulging, costate and asperous on abaxial side; about 12 to 14 pairs and one main center vein;

Veins color: Adaxial same as surrounding tissue; abaxial midrib and center veins nearest RHS 158D, marginal veins nearest RHS 146D and intermediate nearest RHS 155D;

Flower description: Perfect; single; actinomorphic; funnel-form; held outwardly to slightly drooping; persist for normal period, usually one day on plant or as cut flower;

Flower period: Scapes remain effective with flowering beginning late July for about four weeks in Michigan;

Flower size: About 60.0 mm long to exserted style; corolla to about 44.0 mm long and flared to about 52.0 mm across; corolla tube to about 22.0 mm long and 5.0 mm diameter toward base;

Fragrance: None detected;

Floral bracts: Subtending individual flowers; lanceolate to linear; narrowly acute apex, truncate clasping base, margin entire; lustrous adaxial and abaxial; to about 20.0 mm long and 15.0 mm across, decreasing in size distally;

Bract color: Adaxial margin nearest RHS 144A, center nearest RHS NN155B and intermediate nearest RHS 145B; abaxial margin between RHS 138A and RHS 146B, center nearest RHS NN155B and intermediate nearest RHS 146D;

Tepals: Two sets of three; lanceolate with acute apex and fused base;

*Inner set.*—58.0 mm long and 14.0 mm across slightly above fusion; fused in basal 36.0 mm and free in distal 22.0 mm; vitreous along 1.0 mm wide margin.

*Inner set color.*—Adaxial central longitudinal stripe 3.0 mm wide slightly lighter than RHS N87D extending from apex toward base about 25.0 mm;

white margins nearest RHS NN155D and basal 20.0 mm along corolla tube nearest RHS NN155D with faint blush of RHS N87D; abaxial variable between RHS 85D and RHS 76D.

*Outer tepal.*—58.0 mm long and 12.0 mm across slightly above fusion; fused in basal 36.0 mm and free in distal 22.0 mm; not vitreous along margin.

*Outer tepal color*.—Adaxial central longitudinal stripe 3.0 mm wide slightly lighter than RHS N87D extending from apex toward base about 25.0 mm with veins nearest RHS N87D; white margins nearest RHS NN155D and basal 20.0 mm along corolla tube nearest RHS NN155D with faint blush of RHS N87D; abaxial variable between RHS 85D and RHS 76D.

Gynoecium: Single; tri-carpelled; 69.0 mm long;

*Style*.—Single; cylindrical; arcuate upward about 180° in distal 10 mm; about 61.0 mm long and 1.0 mm diameter; color RHS 155A.

*Stigma*.—Tri-lobed, micro-puberulent; about 2.0 mm across and 1.0 mm tall; color nearest RHS 145D.

*Ovary*.—Superior; ellipsoidal; rounded apex and truncate base; lightly longitudinally fluted; about 7.0 mm long and 3.5 mm diameter; color nearest RHS 160D.

Androecium: Six;

*Filaments*.—Cylindrical; glabrous; arcuate upward about 135° in distal 10.0 mm portion; about 51.0 mm long and 0.7 mm diameter; color nearest RHS 155A.

*Anthers*.—Oblong; dorsifixed, longitudinally dehiscent; about 7.0 mm long and 2.5 mm across and 2.0 mm thick; color variable nearest RHS 187C, RHS 85B and RHS 177A.

*Pollen*.—Smaller than 0.1 mm diameter; color nearest RHS 17A.

Flower bud: Clavate; with acute apex and fused tubular base; about 49.0 mm long in total and 12.5 mm wide in bulb portion, tube about 18.0 mm long and 4.0 mm diameter;

Flower bud color: Nearest blend of RHS 85C and RHS 84C;

Pedicel: Cylindrical, glabrous, lustrous; outwardly; to about 10.0 mm long and 2.0 mm diameter;

Pedicel color: Nearest blend of RHS 76C and RHS 76B;

Peduncle: Cylindrical; usually one per mature division and four per plant; slightly glaucous; glabrous; very stiff, rigidly upwardly and straight; length about 213.0 cm long and about 15.0 mm diameter; flowering in upper 66.0 cm with about 90 flowers per scape;

Peduncle color: When flowering nearest blend of RHS 150D and RHS 158D;

Fruit and seeds: Not observed; sterile;

Disease tolerance and resistance: The new plant has not shown any resistance to pests and diseases common to *hostas*. The plant grows best and shows best coloration with plenty of moisture, adequate drainage and light shade, but is able to tolerate some drought when mature. Hardiness at least from USDA zone 3 through 9, and other disease resistance is typical of that of other *hostas*.

It is claimed:

1. A new and distinct ornamental plant cultivar named *Hosta* 'Miss America' as herein described and illustrated.

* * * * *